United States Patent
Legrand

(10) Patent No.: US 7,575,605 B2
(45) Date of Patent: Aug. 18, 2009

(54) DYE COMPOSITION COMPRISING AT LEAST ONE GLYCEROL ESTER AND A PROCESS FOR DYEING KERATIN FIBERS USING THE COMPOSITION

(75) Inventor: Frédéric Legrand, Tokyo (JP)

(73) Assignee: L'Oreal S.A., Paris (FR)

( * ) Notice: Subject to any disclaimer, the term of this patent is extended or adjusted under 35 U.S.C. 154(b) by 158 days.

(21) Appl. No.: 11/393,701

(22) Filed: Mar. 31, 2006

(65) Prior Publication Data

US 2006/0260070 A1    Nov. 23, 2006

Related U.S. Application Data

(60) Provisional application No. 60/681,149, filed on May 16, 2005.

(30) Foreign Application Priority Data

Mar. 31, 2005   (FR) .................................. 05 50839

(51) Int. Cl.
A61Q 5/10 (2006.01)
(52) U.S. Cl. .................. 8/405; 8/406; 8/407; 8/435; 8/552; 8/554; 8/580; 8/582; 8/609
(58) Field of Classification Search .............. 8/405, 8/406, 407, 435, 552, 554, 580, 582, 609
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,075,136 A | 2/1978 | Schaper |
| 4,116,894 A | 9/1978 | Lentz et al. |
| 4,131,576 A | 12/1978 | Iovine et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,240,450 A | 12/1980 | Grollier et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |

(Continued)

FOREIGN PATENT DOCUMENTS

| | | |
|---|---|---|
| DE | 30 30 119 | 2/1982 |
| DE | 38 34 142 | 4/1990 |
| DE | 41 03 292 | 9/1992 |
| DE | 41 27 230 A1 | 2/1993 |
| DE | 101 32 915 A1 | 1/2003 |
| EP | 0 080 976 B1 | 6/1983 |
| EP | 0 122 324 B1 | 10/1984 |
| EP | 0 337 354 B1 | 10/1989 |
| EP | 0 412 706 | 2/1991 |
| EP | 0 714 954 B1 | 6/1996 |
| EP | 0 824 914 | 2/1998 |
| EP | 0 825 200 | 2/1998 |
| EP | 1 048 289 | 11/2000 |
| EP | 1 142 555 | 10/2001 |
| EP | 1 174 450 | 1/2002 |

(Continued)

OTHER PUBLICATIONS

English language Derwent abstract of DE 41 27 230, Feb. 1993.
English language Derwent abstract of DE 101 32 915, Jan. 2003.
English language abstract of EP 0 080 976, Jun. 1983.
English language Derwent abstract of EP 1 232 739, Aug. 2002.
English language Derwent abstract of EP 1 518 547, Mar. 2005.
English language Derwent abstract of FR 2 795 312, Dec. 2001.

(Continued)

*Primary Examiner*—Eisa B Elhilo
(74) *Attorney, Agent, or Firm*—Finnegan, Henderson, Farabow, Garrett & Dunner, LLP

(57) ABSTRACT

Disclosed is a dye composition comprising at least one dye, at least one fatty alcohol, at least one fatty acid ester of glycerol, at least one ether and at least one nonionic and/or anionic surfactant; wherein the dye composition comprises water in an amount of at least 55% by weight, relative to the total weight of the composition. Additionally disclosed is a process for dyeing keratin fibers using such a composition, and also a multi-compartment device comprising the dye composition and an oxidizing composition.

28 Claims, No Drawings

U.S. PATENT DOCUMENTS

| | | | |
|---|---|---|---|
| 4,381,919 A | 5/1983 | Jacquet et al. | |
| 4,422,853 A | 12/1983 | Jacquet et al. | |
| 4,445,521 A | 5/1984 | Grollier et al. | |
| 4,579,732 A | 4/1986 | Grollier et al. | |
| 4,591,610 A | 5/1986 | Grollier | |
| 4,608,250 A | 8/1986 | Jacquet et al. | |
| 4,702,906 A | 10/1987 | Jacquet et al. | |
| 4,719,099 A | 1/1988 | Grollier et al. | |
| 4,719,282 A | 1/1988 | Nadolsky et al. | |
| 4,761,273 A | 8/1988 | Grollier et al. | |
| 4,777,040 A | 10/1988 | Grollier et al. | |
| 4,803,221 A | 2/1989 | Bair | |
| 4,839,166 A | 6/1989 | Grollier et al. | |
| 4,919,923 A | 4/1990 | Hoeffkes et al. | |
| 4,948,579 A | 8/1990 | Jacquet et al. | |
| 4,970,066 A | 11/1990 | Grollier et al. | |
| 4,996,059 A | 2/1991 | Grollier et al. | |
| 5,009,880 A | 4/1991 | Grollier et al. | |
| 5,057,311 A | 10/1991 | Kamegai et al. | |
| 5,089,252 A | 2/1992 | Grollier et al. | |
| 5,139,037 A | 8/1992 | Grollier et al. | |
| 5,196,189 A | 3/1993 | Jacquet et al. | |
| 5,480,459 A | 1/1996 | Mager et al. | |
| 5,494,489 A | 2/1996 | Akram et al. | |
| 5,708,151 A | 1/1998 | Möckli | |
| 5,792,221 A | 8/1998 | Lagrange et al. | |
| 5,958,392 A | 9/1999 | Grollier et al. | |
| 5,990,233 A | 11/1999 | Barron et al. | |
| 6,106,578 A | 8/2000 | Jones | |
| 6,436,151 B2 * | 8/2002 | Cottard et al. | 8/406 |
| 6,540,791 B1 * | 4/2003 | Dias | 8/111 |
| 6,613,315 B1 | 9/2003 | Dupuis | |
| 6,800,098 B1 | 10/2004 | Allard et al. | |
| 6,824,570 B2 | 11/2004 | Vidal et al. | |
| 6,881,230 B2 | 4/2005 | Vidal | |
| 6,884,265 B2 | 4/2005 | Vidal et al. | |
| 6,884,267 B2 | 4/2005 | Vidal et al. | |
| 6,893,471 B2 | 5/2005 | Vidal | |
| 7,001,436 B2 | 2/2006 | Vidal et al. | |
| 7,022,143 B2 | 4/2006 | Vidal et al. | |
| 7,060,110 B2 | 6/2006 | Vidal et al. | |
| 7,077,873 B2 | 7/2006 | David et al. | |
| 7,261,743 B2 | 8/2007 | Plos et al. | |
| 7,326,256 B2 | 2/2008 | Cottard et al. | |
| 2001/0023514 A1 | 9/2001 | Cottard et al. | |
| 2002/0095732 A1 | 7/2002 | Kravtchenko et al. | |
| 2003/0084516 A9 | 5/2003 | Kravtchenko et al. | |
| 2003/0106169 A1 | 6/2003 | Vidal et al. | |
| 2003/0124079 A1 | 7/2003 | Mougin et al. | |
| 2003/0192134 A1 | 10/2003 | Desenne et al. | |
| 2004/0047821 A1 | 3/2004 | Maubru et al. | |
| 2004/0060126 A1 | 4/2004 | Cottard et al. | |
| 2004/0093675 A1 | 5/2004 | Vidal et al. | |
| 2004/0093676 A1 | 5/2004 | Vidal et al. | |
| 2004/0098815 A1 | 5/2004 | Schmenger et al. | |
| 2004/0107513 A1 | 6/2004 | Vidal et al. | |
| 2004/0127692 A1 | 7/2004 | David et al. | |
| 2004/0133995 A1 | 7/2004 | Cottard et al. | |
| 2004/0141943 A1 | 7/2004 | Mougin et al. | |
| 2004/0143911 A1 | 7/2004 | Vidal | |
| 2004/0168263 A1 | 9/2004 | Vidal | |
| 2004/0172771 A1 | 9/2004 | Cottard et al. | |
| 2004/0180030 A1* | 9/2004 | Maubru | 424/70.21 |
| 2004/0187225 A1 | 9/2004 | Vidal et al. | |
| 2004/0200009 A1 | 10/2004 | Vidal | |
| 2004/0205902 A1 | 10/2004 | Cottard et al. | |
| 2004/0216246 A1 | 11/2004 | Cotteret et al. | |
| 2004/0244123 A1 | 12/2004 | Vidal et al. | |
| 2005/0000039 A1 | 1/2005 | Audousset | |
| 2005/0039268 A1 | 2/2005 | Plos et al. | |
| 2005/0081311 A1 | 4/2005 | Schmenger et al. | |

FOREIGN PATENT DOCUMENTS

| | | |
|---|---|---|
| EP | 1 232 739 A1 | 8/2002 |
| EP | 1 413 287 | 4/2004 |
| EP | 1 426 032 | 6/2004 |
| EP | 1 426 039 | 6/2004 |
| EP | 1 428 506 | 6/2004 |
| EP | 1 473 025 | 11/2004 |
| EP | 1 518 547 A1 | 3/2005 |
| FR | 1 400 366 A | 5/1965 |
| FR | 1 492 597 A | 8/1967 |
| FR | 1 583 363 A | 10/1969 |
| FR | 2 077 143 A5 | 10/1971 |
| FR | 2 080 759 A1 | 11/1971 |
| FR | 2 162 025 A1 | 7/1973 |
| FR | 2 190 406 A2 | 2/1974 |
| FR | 2 252 840 A1 | 6/1975 |
| FR | 2 270 846 A1 | 12/1975 |
| FR | 2 280 361 A2 | 2/1976 |
| FR | 2 316 271 A1 | 1/1977 |
| FR | 2 320 330 A1 | 3/1977 |
| FR | 2 336 434 A1 | 7/1977 |
| FR | 2 368 508 A2 | 5/1978 |
| FR | 2 383 660 A1 | 10/1978 |
| FR | 2 393 573 A1 | 1/1979 |
| FR | 2 413 907 A1 | 8/1979 |
| FR | 2 470 596 A1 | 6/1981 |
| FR | 2 505 348 A1 | 11/1982 |
| FR | 2 519 863 A1 | 7/1983 |
| FR | 2 542 997 A1 | 9/1984 |
| FR | 2 598 611 A1 | 11/1987 |
| FR | 2 692 572 A1 | 12/1993 |
| FR | 2 717 076 | 9/1995 |
| FR | 2 795 312 A1 | 12/2000 |
| FR | 2 803 195 | 7/2001 |
| FR | 2 807 650 A1 | 10/2001 |
| FR | 2 822 693 A1 | 10/2002 |
| FR | 2 822 694 A1 | 10/2002 |
| FR | 2 822 696 A1 | 10/2002 |
| FR | 2 822 698 A1 | 10/2002 |
| FR | 2 825 625 A1 | 12/2002 |
| FR | 2 825 702 A1 | 12/2002 |
| FR | 2 829 926 A1 | 3/2003 |
| FR | 2 833 833 | 6/2003 |
| FR | 2 844 269 A1 | 3/2004 |
| GB | 1021400 | 3/1966 |
| GB | 1 331 819 | 9/1973 |
| GB | 1 347 051 | 2/1974 |
| GB | 1 479 786 | 7/1977 |
| GB | 1546809 | 5/1979 |
| WO | WO 95/01772 A1 | 1/1995 |
| WO | WO 95/15144 A1 | 6/1995 |
| WO | WO 99/40893 | 8/1999 |
| WO | WO 00/68282 | 11/2000 |
| WO | WO 02/30370 A1 | 4/2002 |
| WO | WO 02/45674 | 6/2002 |
| WO | WO 02/074271 | 9/2002 |
| WO | WO 02/078660 A1 | 10/2002 |
| WO | WO 02/100369 A2 | 12/2002 |
| WO | WO 02/100834 A1 | 12/2002 |
| WO | WO 2004/019895 A1 | 3/2004 |

OTHER PUBLICATIONS

European Search Report for EP 06 11 1860 (European counterpart application to U.S. Appl. No. 11/393,701, the present application), dated Jul. 18, 2006.

French Search Report for FR 0550839 (Priority Application for U.S. Appl. No. 11/393,701, the present application), dated Nov. 9, 2005.

De Bruin, "Hydrophobically Modified Cellulose Ether for Personal Care." SOFW-Journal Seifen, Oele, Fete, Wachse, Verlag fur Chemische Industri, Augsburg, DE, vol. 120, No. 15, Nov. 30, 1994, pp. 944-946, 948, XP000483287, ISSN: 0942-7694.
Copending U.S. Appl. No. 11/393,694, filed Mar. 31, 2006.
Copending U.S. Appl. No. 11/393,696, filed Mar. 31, 2006.
Copending U.S. Appl. No. 11/393,698, filed Mar. 31, 2006.
Copending U.S. Appl. No. 11/393,700, filed Mar. 31, 2006.
Copending U.S. Appl. No. 11/394,234, filed Mar. 31, 2006.
English language Derwent Abstract of DE 30 30 119, dated Nov. 19, 1987.
English language Derwent Abstract of DE 38 34 142, dated Apr. 12, 1990.
English language Derwent Abstract of DE 41 03 292, dated Feb. 10, 1994.
English language Derwent Abstract of EP 0 122 324, dated Oct. 24, 1984.
English language Derwent Abstract of EP 1 048 289, dated Nov. 2, 2000.
English language Derwent Abstract of FR 2 336 434, dated Jun. 22, 1977.
English language Derwent Abstract of FR 2 470 596, dated Jun. 12, 1981.
European Search Report for EP 06 11 1856 (corresponding European counterpart application to U.S. Appl. No. 11/394,234) dated Jul. 19, 2006, Examiner Loloiu.
European Search Report for EP 06 11 1858 (corresponding European counterpart application to U.S. Appl. No. 11/393,698) dated Jul. 19, 2006, Examiner Loloiu.
European Search Report for EP 06 11 1861 (corresponding European counterpart application to U.S. Appl. No. 11/393,694) dated Jul. 14, 2006, Examiner Loloiu.
French Search Report for FR 05/50835 for U.S. Appl. No. 11/393,700, dated Nov. 3, 2005, Examiner Loloiu.
French Search Report for FR 05/50837 for U.S. Appl. No. 11/393,694, dated Nov. 10, 2005, Examiner Loloiu.
French Search Report for FR 05/50838 for U.S. Appl. No. 11/393,698, dated Nov. 4, 2005, Examiner Loloiu.
French Search Report for FR 05/50841 for U.S. Appl. No. 11/393,696, dated Feb. 14, 2006, Examiner Loloiu.
French Search Report for FR 05/50842 for U.S. Appl. No. 11/394,234, dated Feb. 15, 2006, Examiner Loloiu.
G. Fonnum, J. Bakke and Fk. Hansen, "Associative thickners. Part I: Synthesis, rheology, and aggregation behavior," Colloid Polym. Sci. 271, 380-389 (1993).
Office Action mailed Jan. 7, 2008, in co-pending U.S. Appl. No. 11/393,694, Examiner E. Elhilo.
Office Action mailed Jan. 7, 2008, in co-pending U.S. Appl. No. 11/393,696, Examiner E. Elhilo.
Office Action mailed Jan. 7, 2008, in co-pending U.S. Appl. No. 11/393,698, Examiner E. Elhilo.
Office Action mailed Jan. 7, 2008, in co-pending U.S. Appl. No. 11/393,700, Examiner E. Elhilo.
Office Action mailed Jan. 7, 2008, in co-pending U.S. Appl. No. 11/393,234, Examiner E. Elhilo.
Office Action mailed Jun. 13, 2008, in co-pending U.S. Appl. No. 11/393,698, Examiner E. Elhilo.
Office Action mailed Jun. 18, 2008, in co-pending U.S. Appl. No. 11/393,700, Examiner E. Elhilo.
Office Action mailed Jun. 23, 2008, in co-pending U.S. Appl. No. 11/393,694, Examiner E. Elhilo.
Office Action mailed Jun. 23, 2008, in co-pending U.S. Appl. No. 11/394,234, Examiner E. Elhilo.
Office Action mailed Oct. 22, 2008, in co-pending U.S. Appl. No. 11/393,698, Examiner E. Elhilo.

* cited by examiner

DYE COMPOSITION COMPRISING AT LEAST ONE GLYCEROL ESTER AND A PROCESS FOR DYEING KERATIN FIBERS USING THE COMPOSITION

This application claims benefit of U.S. Provisional Application No. 60/681,149, filed May 16, 2005, the contents of which are incorporated herein by reference. This application also claims benefit of priority under 35 U.S.C. § 119 to French Patent Application No. FR 05 50839, filed Mar. 31, 2005, the contents of which are also incorporated herein by reference.

Disclosed herein is a dye composition comprising at least one dye, at least one fatty alcohol, at least one fatty acid ester of glycerol, at least one ether and at least one nonionic and/or anionic surfactant; wherein the dye composition comprises water in an amount of at least 55% by weight relative to the total weight of the composition.

Also disclosed herein is a process for dyeing keratin fibers using such a composition, and also a multi-compartment device comprising a dye composition and an oxidizing composition.

There are essentially two types of dyeing of keratin fibers, for example, human keratin fibers such as the hair.

The first, known as oxidation dyeing or permanent dyeing, involves using oxidation dye precursors, which are colorless or sparingly colored compounds. When they are placed in contact with an oxidizing agent, these compounds produce, via a process of oxidative condensation taking place within the fiber itself, colored substances that remain trapped in the fibers.

The second, known as direct dyeing or semi-permanent dyeing, is obtained by using colored and coloring compounds that have affinity for the keratin fibers onto which they are applied. This type of dyeing does not require the use of an oxidizing agent to reveal the color, although it is not excluded for this type of agent to be present during the process. The latter case is then referred to as lightening direct dyeing.

The dye compositions of known in the prior art are, in the majority of cases, in the form of liquids, gels or creams, which are mixed, if necessary, before being applied to fibers, with an oxidizing composition.

Dye compositions are usually relatively rich in starting materials, among which are usually found fatty substances, surfactants and/or polymers. These compositions are typically formulated such that they have spreading properties and textures that are easy to work in order to allow quick and easy application to fibers, while at the same time being thick enough not to run beyond the areas that it is desired to color. Furthermore, these compositions should ideally remain stable during the leave-on time on the fibers and ideally be easy to remove by rinsing once the coloration has been obtained.

Large amounts of starting materials may affect the dyeing qualities of such compositions. Less favorable kinetics, a reduced intensity of the shade obtained, poorer homogeneity of the color from one fiber to another and/or depending on the location of the fiber (root/end), etc. may thus be observed.

Disclosed herein are dye compositions which avoid at least one of the abovementioned drawbacks of the current dye compositions, while at the same time preserving at least one of the properties mentioned above.

Disclosed herein are dye compositions comprising, in a medium that is suitable for dyeing keratin fibers:
   at least one dye chosen from oxidation dye precursors and direct dyes;
   at least one fatty alcohol;
   at least one fatty acid ester of glycerol;
   at least one ether of formula R—O—R', in which R and R', which may be identical or different, are each chosen from linear or branched alkyl radicals and linear or branched alkenyl radicals, R and R' being chosen such that the ether of formula R—O—R' is solid at a temperature of less than or equal to 30° C.;
   at least one surfactant chosen from nonionic surfactants and anionic surfactants;
   wherein the composition comprises water in an amount of at least 55% by weight relative to the total weight of the composition.

Also disclosed herein is a process for dyeing keratin fibers using such a composition, and, in some embodiments, in the presence of an oxidizing composition.

Further disclosed herein is a device comprising a first compartment comprising a dye composition according to the disclosure and a second compartment comprising an oxidizing composition.

The composition according to the disclosure may cause less degradation of the dyeing properties and may allow stronger, more homogeneous and more chromatic colorations to be obtained, while at the same time giving the treated fibers good cosmetic properties and limiting their degradation.

The compositions disclosed herein may have an ideal texture for use in the dyeing of human keratin fibers, for example, the hair. For example, they may be creamy, thick enough for quick and easy application, with good removal by rinsing, without, however, running beyond the areas of the hair that it is desired to treat.

Other characteristics and advantages of the present disclosure will emerge more clearly on reading the description and the examples that follow.

In the text below, and unless otherwise indicated, it is pointed out that the limits of ranges of values are included in these ranges.

When mention is made herein of a compound with a fatty chain, this chain is a linear or branched, saturated or unsaturated hydrocarbon-based chain comprising from 8 to 30 carbon atoms, for example, 10 to 24 carbon atoms.

As discussed above, the composition of the present disclosure is suitable for dyeing keratin fibers, for example, human keratin fibers, and further, for example, the hair.

The dye composition according to the present disclosure comprises water in an amount of at least 55% by weight relative to the total weight of the dye composition. According to one embodiment, the water content in the composition is at least 60% by weight relative to the total weight of the dye composition.

The composition disclosed herein comprises at least one fatty alcohol. In at least one embodiment, the at least one fatty alcohol is non-oxyalkylenated and non-glycerolated.

The at least one fatty alcohol may be chosen, for example, from linear or branched, saturated or unsaturated $C_8$-$C_{30}$, for example, $C_{10}$-$C_{24}$, such as $C_{12}$-$C_{24}$, alcohols, optionally comprising at least one other hydroxyl group. Examples that may be mentioned include oleyl alcohol, lauryl alcohol, palmityl alcohol, myristyl alcohol, behenyl alcohol, stearyl alcohol, linoleyl alcohol, linolenyl alcohol, capryl alcohol and arachidonyl alcohol, and mixtures thereof.

According to at least one embodiment, the at least one fatty alcohol is present in an amount ranging from 0.1% to 30% by weight, such as from 0.5 to 20% by weight, relative to the total weight of the composition.

In another embodiment, the composition disclosed herein may comprise another fatty substance other than the abovementioned fatty alcohols. Thus, the composition may comprise as a fatty substance at least one compound chosen from non-oxyalkylenated and non-glycerolated fatty acid amides, mineral oils and plant oils, and mixtures thereof.

The fatty acid amides may, for example, be chosen from compounds derived from an alkanolamine and from a $C_8$-$C_{30}$ fatty acid. They may be, for example, chosen from amides of a $C_2$-$C_{10}$ alkanolamine and of a $C_{14}$-$C_{30}$ fatty acid, and further, for example, from amides of a $C_2$-$C_{10}$ alkanolamine and of a $C_{14}$-$C_{22}$ fatty acid.

In one embodiment, the fatty acid amide is chosen from:
oleic acid diethanolamide, such as the amide sold under the trade name Mexanyl® GT by the company Chimex,
myristic acid monoethanolamide, such as the amide sold under the trade name Comperlan® MM by the company Cognis,
soybean fatty acid diethanolamide, such as the amide sold under the trade name Comperlan® VOD by the company Cognis,
stearic acid ethanolamide, such as the amide sold under the trade name Monamid® S by the company Uniqema,
oleic acid monoisopropanolamide, such as the amide sold under the trade name Witcamide® 61 by the company Witco,
linoleic acid diethanolamide, such as the amide sold under the trade name Purton® SFD by the company Zschimmer Schwarz,
stearic acid monoethanolamide, such as the amide sold under the trade name Monamid® 972 by the company ICI/Uniqema,
behenic acid monoethanolamide, such as the amide sold under the trade name Incromide® BEM from Croda,
isostearic acid monoisopropanolamide, such as the amide sold under the trade name Witcamide® SPA by the company Witco,
erucic acid diethanolamide, such as the amide sold under the trade name erucic acid diethanolamide by the company Stéarineries Dubois,
ricinoleic acid monoethanolamide, such as the amide sold under the trade name ricinoleic monoethanolamide by the company Stéarineries Dubois.

Liquid paraffin is an example of a mineral oil that may be used as fatty substance in the composition.

As regards the plant oils, non-limiting mention may be made of avocado oil, olive oil or liquid jojoba wax.

According to at least one embodiment, the at least one fatty substance other than the abovementioned fatty alcohols is present in an amount ranging from 0.1% to 30% by weight, such as from 0.5% to 20% by weight, relative to the total weight of the composition.

Additionally, the composition disclosed herein comprises at least one fatty acid ester of glycerol.

In one embodiment, the at least one fatty acid ester of glycerol is chosen from esters of oleic acid, lauric acid, palmitic acid, myristic acid, behenic acid, stearic acid, linoleic acid, linolenic acid, capric acid, arachidic acid or arachidonic acid, and mixtures thereof.

According to at least one embodiment, the at least one fatty acid ester of glycerol is present in an amount ranging from 0.1% to 20% by weight, such as from 0.5% to 15% by weight, relative to the weight of the composition.

The dye composition disclosed herein comprises at least one ether of formula R—O—R' wherein R and R', which may be identical or different, are each chosen from linear or branched alkyl or alkenyl radicals, R and R' being chosen such that the at least one ether of formula R—O—R' is solid at a temperature of less than or equal to 30° C.

For example, the ether is chosen from compounds wherein R and R', which may be identical or different, are each chosen from linear or branched $C_{10}$-$C_{30}$, for example, $C_{14}$-$C_{24}$, alkyl or alkenyl radicals.

According to one embodiment, R and R', which may be identical or different, are chosen from radicals derived from oleyl alcohol (C18), lauryl alcohol (C12), palmityl alcohol (C16), myristyl alcohol (C14), behenyl alcohol (C22), stearyl alcohol (C18), linoleyl alcohol (C18), linolenyl alcohol (C18) or arachidyl alcohol (C20).

In one embodiment, R and R' may be identical.

In another embodiment, R and R' may both be chosen from stearyl radicals.

The dialkyl ethers that may be used herein may be soluble or insoluble in the compositions. In at least one embodiment, they are insoluble.

These compounds may be prepared according to the process described in German Patent Application No. DE 41 27 230.

A distearyl ether that may be used, for example, is sold under the name CUTINA KE 3178 by the company Henkel.

The at least one ether of formula R—O—R' may, for example, may be present in an amount ranging from 0.1% to 10% by weight, such as from 0.2 to 6% by weight, relative to the total weight of the composition.

The composition disclosed herein comprises at least one surfactant chosen from nonionic surfactants and anionic surfactants.

For example, the nonionic surfactants may be chosen from oxyalkylenated or glycerolated compounds, and mixtures thereof.

In at least one embodiment, the nonionic surfactant may be chosen from:
oxyalkylenated or glycerolated fatty alcohols;
oxyalkylenated alkylphenols wherein the alkyl chain is $C_8$-$C_{18}$;
oxyalkylenated or glycerolated fatty amides;
oxyalkylenated plant oils;
optionally oxyalkylenated $C_6$-$C_{30}$ acid esters of sorbitan;
optionally oxyalkylenated fatty acid esters of sucrose;
fatty acid esters of polyethylene glycol;
($C_6$-$C_{30}$)alkylpolyglycosides;
N—($C_6$-$C_{30}$)alkylglucamine derivatives;
amine oxides such as ($C_{10}$-$C_{14}$)alkylamine oxides or N-acylaminopropylmorpholine oxides;
copolymers of ethylene oxide and of propylene oxide; and mixtures thereof.

In at least one embodiment, the mean number of oxyalkylene units may range from 2 to 150 units. In at least one further embodiment, they are oxyethylene or oxypropylene units, or mixtures thereof.

The polyglycerolated surfactants may comprise on average 1 to 20, for example, 1.5 to 5, glycerol groups.

According to one embodiment, the composition comprises at least one nonionic surfactant chosen from oxyalkylenated or glycerolated $C_6$-$C_{30}$ alcohols.

The at least one anionic surfactant may be chosen from:
($C_6$-$C_{30}$)alkyl sulfates, ($C_6$-$C_{30}$)alkyl ether sulfates, ($C_6$-$C_{30}$)alkylamido ether sulfates, alkylaryl polyether sulfates, monoglyceride sulfates;
($C_6$-$C_{30}$)alkylsulfonates, ($C_6$-$C_{30}$)alkylamide sulfonates, ($C_6$-$C_{30}$)alkylaryl sulfonates, α-olefin sulfonates, paraffin sulfonates;
($C_6$-$C_{30}$)alkyl phosphates;
($C_6$-$C_{30}$)alkyl sulfosuccinates, ($C_6$-$C_{30}$)alkyl ether sulfosuccinates, ($C_6$-$C_{30}$)alkylamide sulfosuccinates;
($C_6$-$C_{30}$)alkyl sulfoacetates;

($C_6$-$C_{24}$)acyl sarcosinates;
($C_6$-$C_{24}$)acyl glutamates;
($C_6$-$C_{30}$)alkylpolyglycoside carboxylic ethers; ($C_6$-$C_{30}$) alkylpolyglycoside sulfosuccinates;
($C_6$-$C_{30}$)alkyl sulfosuccinamates;
($C_6$-$C_{24}$)acyl isethionates;
N—($C_6$-$C_{24}$)acyl taurates;
fatty acid salts;
($C_8$-$C_{20}$)acyl lactylates;
($C_6$-$C_{30}$)alkyl-D-galactoside uronic acid salts;
polyoxyalkylenated ($C_6$-$C_{30}$)alkyl ether carboxylic acid salts, polyoxyalkylenated ($C_6$-$C_{30}$)alkylaryl ether carboxylic acid salts, polyoxyalkylenated ($C_6$-$C_{30}$)alkylamido ether carboxylic acid salts;
and mixtures thereof.

In at least one embodiment, the anionic surfactants may be in the form of salts in the composition disclosed herein, for example, salts of alkali metals, for instance sodium; salts of alkaline-earth metals, for instance magnesium; ammonium salts; amine salts; and amino alcohol salts. Depending on the conditions, the anionic surfactants may also be in the acid form thereof.

It should be noted that the alkyl or acyl radicals of these various compounds may comprise, for example, from 12 to 20 carbon atoms. In at least one embodiment, the aryl radical is chosen from phenyl and benzyl groups.

Furthermore, the polyoxyalkylenated anionic surfactants may comprise from 2 to 50 alkylene oxide, for example, ethylene oxide groups.

According to one embodiment, the at least one anionic surfactant may be chosen from fatty acid salts and from surfactants comprising at least one sulfate group.

In at least one embodiment the at least one surfactant chosen from nonionic surfactants and anionic surfactants is present in an amount ranging from 0.01% to 40% by weight, such as from 0.5% to 30% by weight, relative to the total weight of the composition.

The composition disclosed herein also comprises at least one dye chosen from oxidation dye precursors and direct dyes.

The at least one oxidation dye precursor may be chosen from oxidation bases and couplers, and mixtures thereof.

The oxidation bases may be, for example, chosen from the oxidation bases conventionally used for oxidation dyeing, for example, para-phenylenediamines, bis(phenyl)alkylenediamines, para-aminophenols, ortho-aminophenols and heterocyclic bases, and the addition salts thereof with an acid or with an alkaline agent.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy)pyrrolidine, and the addition salts thereof with an acid or with an alkaline agent.

The para-phenylenediamines may be chosen, for example, from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid or with an alkaline agent.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,5-dioxaoctane, and the addition salts thereof with an acid or with an alkaline agent.

The para-aminophenols may be chosen, for example, from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

The ortho-aminophenols may be chosen, for example, from 2-aminophenol, 2-amino-5-methylphenol, 2-amino-6-methylphenol and 5-acetamido-2-aminophenol, and the addition salts thereof with an acid or with an alkaline agent.

The heterocyclic bases may be chosen, for example, from pyridine derivatives, such as 2,3-diamino-6-methoxypyridine; pyrimidine derivatives such as 2,4,5,6-tetraaminopyrimidine or 4-hydroxy-2,5,6-triaminopyrimidine; and pyrazole derivatives such as 1N-β-hydroxyethyl-4,5-diaminopyrazole; and the addition salts thereof with an acid or with an alkaline agent.

When used, the at least one oxidation base may be present in an amount ranging from 0.0005% to 12% by weight, such as from 0.005% to 6% by weight, relative to the total weight of the composition.

The composition may also comprise, combined with at least one oxidation base, at least one coupler so as to modify or to enrich with tints the shades obtained.

The at least one coupler may be chosen from the couplers conventionally used in oxidation dyeing, for example, meta-phenylenediamines, meta-aminophenols, meta-diphenols and heterocyclic couplers, and the addition salts thereof with an acid or with an alkaline agent.

In at least one embodiment, the at least one coupler may be chosen from 2-methyl-5-aminophenol, 5-N-(β-hydroxyethyl)amino-2-methylphenol, 3-aminophenol, 2-methyl-5-amino-6-chlorophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2-amino-3-hydroxypyridine, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methyl-pyrazolo[1,5-a]benzimidazole, and the addition salts thereof with an acid or with an alkaline agent.

When present, the at least one coupler may be present in an amount ranging from 0.0001% to 15% by weight, for example, from 0.005% to 12% by weight, relative to the total weight of the composition. In one embodiment, the at least one coupler may be present in an amount ranging from 0.01% to 10% by weight relative to the total weight of the composition.

In general, the addition salts with an acid may be chosen from the hydrochlorides, hydrobromides, sulfates, citrates, succinates, tartrates, tosylates, benzenesulfonates, lactates and acetates.

The at least one direct dye may be chosen from nonionic, cationic and anionic dyes.

Non-limiting examples of the at least one direct dye that may be mentioned include nitrobenzene dyes, azo, azomethine, methine, tetraazapentamethine, anthraquinone, naphthoquinone, benzoquinone, phenothiazine, indigoid, xanthene, phenanthridine, phthalocyanin and triarylmethane-based dyes and natural dyes, alone or as mixtures.

The at least one direct dye may be chosen, for example, from the following red or orange nitrobenzene dyes:
  1-hydroxy-3-nitro-4-N-(γ-hydroxypropyl)aminobenzene,
  N-(β-hydroxyethyl)amino-3-nitro-4-aminobenzene,
  1-amino-3-methyl-4-N-(β-hydroxyethyl)amino-6-nitrobenzene,
  1-hydroxy-3-nitro-4-N-(β-hydroxyethyl)aminobenzene,
  1,4-diamino-2-nitrobenzene,
  1-amino-2-nitro-4-methylaminobenzene,
  N-(β-hydroxyethyl)-2-nitro-para-phenylenediamine,
  1-amino-2-nitro-4-(β-hydroxyethyl)amino-5-chlorobenzene,
  2-nitro-4-aminodiphenylamine,
  1-amino-3-nitro-6-hydroxybenzene,
  1-(β-aminoethyl)amino-2-nitro-4-(β-hydroxyethyloxy)benzene,
  1-(β,γ-dihydroxypropyl)oxy-3-nitro-4-(β-hydroxyethyl)aminobenzene,
  1-hydroxy-3-nitro-4-aminobenzene,
  1-hydroxy-2-amino-4,6-dinitrobenzene,
  1-methoxy-3-nitro-4-(β-hydroxyethyl)aminobenzene,
  2-nitro-4'-hydroxydiphenylamine, and
  1-amino-2-nitro-4-hydroxy-5-methylbenzene.

The at least one direct dye may also be chosen from yellow and green-yellow nitrobenzene direct dyes; non-limiting mention may be made, for example, of the compounds chosen from:
  1-β-hydroxyethyloxy-3-methylamino-4-nitrobenzene,
  1-methylamino-2-nitro-5-(β,γ-dihydroxypropyl)oxybenzene,
  1-(β-hydroxyethyl)amino-2-methoxy-4-nitrobenzene,
  1-(β-aminoethyl)amino-2-nitro-5-methoxybenzene,
  1,3-di(β-hydroxyethyl)amino-4-nitro-6-chlorobenzene,
  1-amino-2-nitro-6-methylbenzene,
  1-(β-hydroxyethyl)amino-2-hydroxy-4-nitrobenzene,
  N-(β-hydroxyethyl)-2-nitro-4-trifluoromethylaniline,
  4-(β-hydroxyethyl)amino-3-nitrobenzenesulfonic acid,
  4-ethylamino-3-nitrobenzoic acid,
  4-(β-hydroxyethyl)amino-3-nitrochlorobenzene,
  4-(β-hydroxyethyl)amino-3-nitromethylbenzene,
  4-(β,γ-dihydroxypropyl)amino-3-nitrotrifluoromethylbenzene,
  1-(β-ureidoethyl)amino-4-nitrobenzene,
  1,3-diamino-4-nitrobenzene,
  1-hydroxy-2-amino-5-nitrobenzene,
  1-amino-2-[tris(hydroxymethyl)methyl]amino-5-nitrobenzene,
  1-(β-hydroxyethyl)amino-2-nitrobenzene, and
  4-(β-hydroxyethyl)amino-3-nitrobenzamide.

The at least one direct dye may also be chosen from blue or violet nitro-benzene direct dyes, for instance:
  1-(β-hydroxyethyl)amino-4-N,N-bis(β-hydroxyethyl)amino-2-nitrobenzene,
  1-(γ-hydroxypropyl)amino-4,N,N-bis(β-hydroxyethyl)amino-2-nitrobenzene,
  1-(β-hydroxyethyl)amino-4-(N-methyl-N-β-hydroxyethyl)amino-2-nitrobenzene,
  1-(β-hydroxyethyl)amino-4-(N-ethyl-N-β-hydroxyethyl)amino-2-nitrobenzene,
  1-(β,γ-dihydroxypropyl)amino-4-(N-ethyl-N-β-hydroxyethyl)amino-2-nitrobenzene,
  2-nitro-para-phenylenediamines having the following formula:

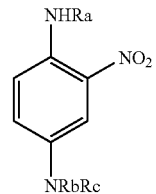

wherein:
  Rb is chosen from $C_1$-$C_4$ alkyl radicals and β-hydroxyethyl, β-hydroxypropyl or γ-hydroxypropyl radicals;
  Ra and Rc, which may be identical or different, are each chosen from β-hydroxyethyl, β-hydroxypropyl, γ-hydroxypropyl or β,γ-dihydroxypropyl radicals,
  wherein at least one of the radicals Rb, Rc or Ra is chosen from γ-hydroxypropyl radicals and
  wherein Ra and Rc are not both chosen from β-hydroxyethyl radicals when Rb is a γ-hydroxypropyl radical, such as those described in French Patent No. FR 2 692 572.

Among the azo direct dyes that may be used, non-limiting mention may be made of the cationic azo dyes described in PCT Patent Publication Nos. WO 95/15144, WO 95/01772, WO 02/078 660, WO 02/100 834, and WO 02/100 369; European Patent Application No. EP 714 954, French Patent Application Nos. FR 2 822 696, FR 2 825 702, FR 2 825 625, FR 2 822 698, FR 2 822 693, FR 2 822 694, FR 2 829 926, FR 2 807 650, and FR 2 844 269.

Among these compounds, non-limiting mention may be made of the following dyes:
  1,3-dimethyl-2-[[4-(dimethylamino)phenyl]azo]-1H-imidazolium chloride,
  1,3-dimethyl-2-[(4-aminophenyl)azo]-1H-imidazolium chloride,
  1-methyl-4-[(methylphenylhydrazono)methyl]pyridinium methyl sulfate.

Among the azo direct dyes that may also be mentioned, for example, are the following dyes described in the Colour Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Non-limiting mention may also be made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Among the quinone direct dyes that may be mentioned are, for example, the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds:

- 1-N-methylmorpholiniumpropylamino-4-hydroxyanthraquinone
- 1-aminopropylamino-4-methylaminoanthraquinone
- 1-aminopropylaminoanthraquinone
- 5-β-hydroxyethyl-1,4-diaminoanthraquinone
- 2-aminoethylaminoanthraquinone
- 1,4-bis(β,γ-dihydroxypropylamino)anthraquinone.

Among the azine dyes that may be mentioned, for example, are the following compounds: Basic Blue 17, Basic Red 2.

Among the cationic methine direct dyes, non-limiting mention may also be made of Basic Red 14, Basic Yellow 13 and Basic Yellow 29.

Among the triarylmethane dyes that may be used, non-limiting mention may be made of the following compounds: Basic Green 1, Acid Blue 9, Basic Violet 3, Basic Violet 14, Basic Blue 7, Acid Violet 49, Basic Blue 26, Acid Blue 7.

Among the indoamine dyes that may be used, non-limiting mention may be made of the following compounds:

- 2-β-hydroxyethylamino-5-[bis(β-4'-hydroxyethyl)amino]anilino-1,4-benzoquinone;
- 2-β-hydroxyethylamino-5-(2'-methoxy-4'-amino)anilino-1,4-benzoquinone;
- 3-N(2'-chloro-4'-hydroxy)phenylacetylamino-6-methoxy-1,4-benzoquinoneimine;
- 3-N(3'-chloro-4'-methylamino)phenylureido-6-methyl-1,4-benzoquinoneimine;
- 3-[4'-N-(ethylcarbamylmethyl)amino]phenylureido-6-methyl-1,4-benzoquinoneimine.

The composition may also comprise at least one natural direct dye, for instance lawsone, juglone, alizarin, purpurin, carminic acid, kermesic acid, purpurogallin, protocatechaldehyde, indigo, isatin, curcumin, spinulosin or apigenidin. Extracts or decoctions comprising these natural dyes, for example, henna-based poultices or extracts, may also be used.

The at least one direct dye, when present, may be present in an amount ranging from 0.0005% to 15% by weight relative to the weight of the composition, for example, from 0.005% to 12% by weight relative to the total weight of the composition. In one embodiment, the at least one direct dye may be present in an amount ranging from 0.01% to 5% by weight relative to the total weight of the composition.

The composition disclosed herein may also comprise at least one basifying agent.

Among the basifying agents that may be mentioned, for example, are aqueous ammonia, alkali metal carbonates, $C_2$-$C_{10}$ alkanolamines such as monoethanolamine, diethanolamine and triethanolamine and also derivatives thereof, oxyethylenated and/or oxypropylenated hydroxyalkylamines and ethylenediamines, sodium hydroxide, potassium hydroxide, alkali metal or alkaline-earth metal silicates and the compounds having the following formula:

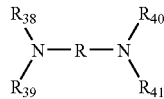

wherein

R is a propylene residue optionally substituted with a hydroxyl group or a $C_1$-$C_4$ alkyl radical;

$R_{38}$, $R_{39}$, $R_{40}$ and $R_{41}$, which may be identical or different, are each chosen from hydrogen atoms, $C_1$-$C_4$ alkyl radicals and $C_1$-$C_4$ hydroxyalkyl radicals.

For example, the basifying agent may be chosen from aqueous ammonia, alkanolamines and combinations of alkanolamines with alkali metal or alkaline-earth metal silicates.

According to one embodiment, the composition does not comprise aqueous ammonia as basifying agent.

The pH of the disclosed composition may, for example, be adjusted by using acidifying agents, for instance mineral or organic acids such as hydrochloric acid, orthophosphoric acid or sulfuric acid, carboxylic acids, for instance acetic acid, tartaric acid, citric acid or lactic acid, or sulfonic acids.

For example, the content of basifying and/or acidifying agent is such that the pH of the dye composition ranges from 3 to 12, for example from 4 to 11 and, further for example, from 7 to 11.

The composition disclosed herein may also comprise at least one cationic or amphoteric substantive polymers.

As used herein, the term "cationic polymer" denotes any polymer comprising cationic groups and/or groups that may be ionized into cationic groups.

Such polymers may be chosen from those already known per se as improving the cosmetic properties of the hair, for example, those described in European Patent Application No. EP-A-337 354 and in French Patent Nos. FR-2 270 846, 2 383 660, 2 598 611, 2 470 596 and 2 519 863.

The at least one cationic polymer may be chosen from those comprising units comprising primary, secondary, tertiary and/or quaternary amine groups, which may either form part of the main polymer chain or may be borne by a side substituent directly attached thereto.

The cationic polymers used may, for example, have a number-average molecular mass ranging from 500 to $5 \times 10^6$, for example, from $10^3$ to $3 \times 10^6$.

Among the cationic polymers that may be mentioned are, for example, polymers of the polyamine, polyamino amide and polyquaternary ammonium type, for example, described in French Patents Nos. 2 505 348 and 2 542 997.

Among the cationic polymers, non-limiting mention may be made of:

(1) homopolymers or copolymers derived from acrylic or methacrylic esters or amides and comprising at least one of the units of formula (I), (II), (III) or (IV) below:

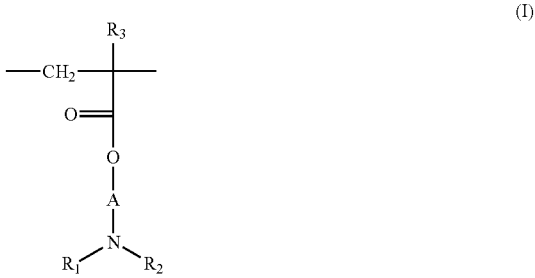

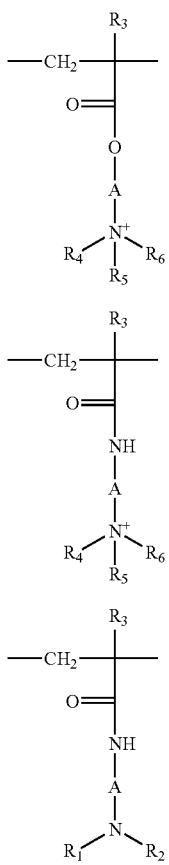

wherein:

R$_3$, which may be identical or different, is chosen from hydrogen atoms and CH$_3$ radicals;

A, which may be identical or different, is chosen from linear or branched alkyl groups of 1 to 6 carbon atoms, for example, 2 or 3 carbon atoms, and hydroxyalkyl groups of 1 to 4 carbon atoms;

R$_4$, R$_5$ and R$_6$, which may be identical or different, are each chosen from benzyl radicals and from alkyl groups comprising from 1 to 18 carbon atoms; for example, from 1 to 6 carbon atoms;

R$_1$ and R$_2$, which may be identical or different, are each chosen from hydrogen and from alkyl groups comprising from 1 to 6 carbon atoms, for example methyl or ethyl;

X is an anion derived from an inorganic or organic acid, such as a methosulfate anion or a halide such as chloride or bromide.

The polymers of family (1) above may also comprise, for example, at least one unit derived from comonomers which may be chosen from the family of acrylamides, methacrylamides, diacetone acrylamides, acrylamides and methacrylamides substituted on the nitrogen with lower (C$_1$-C$_4$) alkyls, acrylic or methacrylic acids or esters thereof, vinyllactams such as vinylpyrrolidone or vinylcaprolactam, and vinyl esters.

Thus, among these polymers of family (1), non-limiting mention may be made of:

copolymers of acrylamide and of dimethylaminoethyl methacrylate quaternized with dimethyl sulfate or with a dimethyl halide, such as the product sold under the name HERCOFLOC by the company Hercules, the copolymers of acrylamide and of methacryloyloxyethyltrimethylammonium chloride described, for example, in European Patent Application No. EP-A-080 976 and sold under the name BINA QUAT P 100 by the company Ciba Geigy, the copolymer of acrylamide and of methacryloyloxyethyltrimethylammonium methosulfate sold under the name RETEN by the company Hercules, quaternized or non-quaternized vinylpyrrolidone/dialkylaminoalkyl acrylate or methacrylate copolymers, such as the products sold under the name "Gafquat" by the company ISP, for instance "Gafquat 734" or "Gafquat 755", or alternatively the products known as "Copolymer 845, 958 and 937". These polymers are described in detail in French Patent Nos. 2 077 143 and 2 393 573, dimethylaminoethyl methacrylate/vinylcaprolactam/vinylpyrrolidone terpolymers, such as the product sold under the name GAFFIX VC 713 by the company ISP, vinylpyrrolidone/methacrylamidopropyldimethylamine copolymers sold, for example, under the name STYLEZE CC 10 by ISP, and quaternized vinylpyrrolidone/dimethylaminopropyl methacrylamide copolymers such as the product sold under the name "Gafquat HS 100" by the company ISP.

(2) The cellulose ether derivatives comprising quaternary ammonium groups, which are described in French Patent No.1 492 597, for example, the polymers sold under the names "JR" (JR 400, JR 125, JR 30M) or "LR" (LR 400, LR 30M) by the company Union Carbide Corporation. These polymers are also defined in the CTFA dictionary as hydroxyethylcellulose quaternary ammoniums that have reacted with an epoxide substituted with a trimethylammonium group.

(3) Cationic cellulose derivatives such as the copolymers of cellulose or cellulose derivatives grafted with a water-soluble quaternary ammonium monomer, described in U.S. Pat. No. 4,131,576, such as hydroxyalkylcelluloses, for instance hydroxymethyl-, hydroxyethyl- or hydroxypropylcelluloses grafted, for example, with a methacryloylethyltrimethylammonium, methacrylamidopropyltrimethylammonium or dimethyldiallylammonium salt.

The commercial products corresponding to this definition are, for example, the products sold under the name CELQUAT L 200 and CELQUAT H 100 by the company National Starch.

(4) The cationic guar gums are described, for example, in U.S. Pat. Nos. 3,589,578 and 4,031,307, such as guar gums comprising trialkylammonium cationic groups. Use is made, for example, of guar gums modified with a salt (e.g., chloride) of 2,3-epoxypropyltrimethylammonium.

Such products are sold, for example, under the trade names JAGUAR C13S, JAGUAR C15, JAGUAR C17 and JAGUAR C162 by the company Meyhall.

(5) Polymers comprising piperazinyl units and of divalent alkylene or hydroxyalkylene radicals comprising straight or branched chains, optionally interrupted by oxygen, sulfur or nitrogen atoms or by aromatic or heterocyclic rings, and also the oxidation and/or quaternization products of these polymers. Such polymers are described, for example, in French Patent Nos. 2 162 025 and 2 280 361.

(6) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyidiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they comprise at least one tertiary amine functions, they can be quaternized. Such polymers are described, for example, in French Patent Nos. 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers wherein the alkyl radical comprises from 1 to 4 carbon atoms, for example, methyl, ethyl or propyl. Such polymers are described, for example, in French Patent No.1 583 363.

Among these derivatives, non-limiting mention may be made of the adipic acid/dimethylaminohydroxypropyl/diethylenetriamine polymers sold under the name "Cartaretine F, F4 or F8" by the company Sandoz.

(8) The polymers obtained by reaction of a polyalkylene polyamine comprising two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described, for example, in U.S. Pat. Nos. 3,227,615 and 2,961,347.

Polymers of this type are sold, for example, under the name "Hercosett 57" by the company Hercules Inc. or alternatively under the name "PD 170" or "Delsette 101 " by the company Hercules in the case of the adipic acid/epoxypropyl/diethylenetriamine copolymer.

(9) Cyclopolymers of alkyldiallylamine or of dialkyldiallylammonium, such as the homopolymers or copolymers comprising, as main constituent of the chain, units corresponding to formula (V) or (VI):

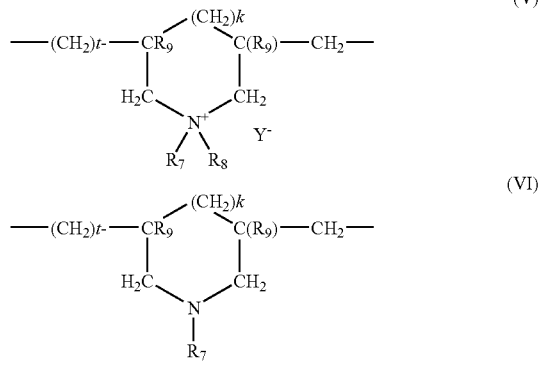

wherein:
k and t are chosen from 0 or 1, the sum k+t being equal to 1;
$R_9$ is chosen from hydrogen atoms and methyl radicals;
$R_7$ and $R_8$, which may be the same or different, are each chosen from alkyl groups comprising from 1 to 6 carbon atoms, hydroxyalkyl groups wherein the alkyl group comprises from 1 to 5 carbon atoms, and
lower ($C_1$-$C_4$) amidoalkyl groups,
or $R_7$ and $R_8$, together with the nitrogen atom to which they are attached, can form heterocyclic groups such as piperidyl or morpholinyl;

For example, $R_7$ and $R_8$, which may be the same or different, are each chosen from alkyl groups having from 1 to 4 carbon atoms;
$Y^-$ is chosen from an anion such as bromide, chloride, acetate, borate, citrate, tartrate, bisulfate, bisulfite, sulfate or phosphate. These polymers are described, for example, in French Patent No. 2 080 759 and in its Certificate of Addition 2 190 406.

Among the polymers defined above, non-limiting mention may be made of the dimethyldiallylammonium chloride homopolymer sold under the name "Merquat 100" by the company Calgon (and its homologues of low weight-average molecular mass) and the copolymers of diallyidimethylammonium chloride and of acrylamide, sold under the name "Merquat 550".

(10) The quaternary diammonium polymer comprising repeating units corresponding to the formula:

wherein:
$R_{10}$, $R_{11}$, $R_{12}$ and $R_{13}$, which may be identical or different, are each chosen from aliphatic, alicyclic or arylaliphatic radicals comprising from 1 to 20 carbon atoms and lower hydroxyalkylaliphatic radicals, or
alternatively $R_{10}$, $R_{11}$, $R_{12}$ and $R_{13}$, together or separately, constitute, with the nitrogen atoms to which they are attached, heterocycles optionally comprising a second hetero atom other than nitrogen, or
alternatively $R_{10}$, $R_{11}$, $R_{12}$ and $R_{13}$, which may be identical or different, are each chosen from
linear or branched $C_1$-$C_6$ alkyl radicals substituted with a nitrile, ester, acyl or amide group and
groups —CO—O—$R_{14}$-D or —CO—NH—$R_{14}$-D wherein $R_{14}$ is chosen from alkylenes and D is chosen from quaternary ammonium groups;
$A_1$ and $B_1$, which may be identical or different, are each chosen from polymethylene groups comprising from 2 to 20 carbon atoms which may be linear or branched, saturated or unsaturated, and which may comprise, linked to or intercalated in the main chain, at least one aromatic rings or at least one oxygen or sulfur atoms or sulfoxide, sulfone, disulfide, amino, alkylamino, hydroxyl, quaternary ammonium, ureido, amide or ester groups, and
$X^-$ is chosen from anions derived from an inorganic or organic acid;
$A_1$, $R_{10}$ and $R_{12}$ can form, with the two nitrogen atoms to which they are attached, a piperazine ring; in addition, if $A_1$ is chosen from linear or branched, saturated or unsaturated alkylene or hydroxyalkylene radicals, $B_1$ may also be chosen from —($CH_2$)$_n$—CO-D-OC—($CH_2$)$_n$— wherein D is chosen from:

a) a glycol residue of formula: —O-Z-O—, wherein Z is chosen from linear or branched hydrocarbon-based radicals and groups corresponding to one of the following formulae:

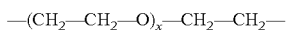

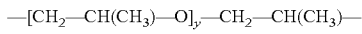

wherein x and y are chosen from integers ranging from 1 to 4, representing a defined and unique degree of polymerization or x and y are chosen from numbers ranging from 1 to 4 representing an average degree of polymerization;

b) a bis-secondary diamine residue such as a piperazine derivative;

c) a bis-primary diamine residue of formula: —NH—Y—NH—, wherein Y is chosen from linear or branched hydrocarbon-based radicals and divalent radicals

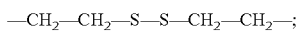

d) a ureylene group of formula: —NH—CO—NH—.

For example, $X^-$ is chosen from anions such as chloride or bromide.

These polymers may, for example, have a number-average molecular mass of between 1000 and 100 000.

Polymers of this type are described in, for example, in French Patent Nos. 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

In one embodiment, it may be possible to use polymers that comprise repeating units corresponding to the following formula (VIII):

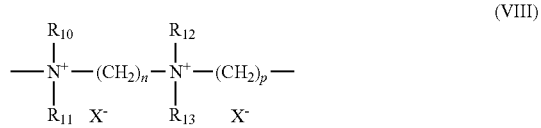

wherein $R_{10}$, $R_{11}$, $R_{12}$ and $R_{13}$, which may be identical or different, are each chosen from alkyl or hydroxyalkyl radicals comprising from 1 to 4 carbon atoms, n and p are chosen from integers ranging from 2 to 20, and $X^-$ is an anion derived from a mineral or organic acid.

(11) Polyquaternary ammonium polymers consisting of units of formula (IX)

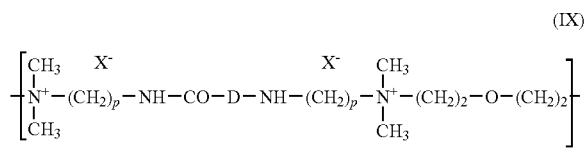

wherein p is chosen from an integer ranging from 1 to 6, D may be a bond or a group —$(CH_2)_r$—CO— wherein r is chosen from number equal to 4 or 7, and $X^-$ is an anion.

Such polymers may be prepared according to the processes described in U.S. Pat. Nos. 4,157,388, 4,702,906 and 4,719, 282. They are further described in European Patent Application No. EP-A-122 324.

Among these polymers, examples that may be mentioned, for example, include the products "Mirapol A 15", "Mirapol AD1", "Mirapol AZ1" and "Mirapol 175" sold by the company Miranol.

(12) Quaternary polymers of vinylpyrrolidone and of vinylimidazole, for instance the products sold under the names LUVIQUAT FC 905, FC 550 and FC 370 by the company BASF.

(13) Polyamines such as POLYQUART H sold by Henkel, which is given under the reference name "Polyethylene glycol (15) tallow polyamine" in the CTFA dictionary.

(14) Crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, for example, methylenebisacrylamide. A crosslinked acrylamide/methacryloyloxyethyltrimethylammonium chloride copolymer (20/80 by weight) in the form of a dispersion comprising 50% by weight of said copolymer in mineral oil can be used, for example. This dispersion is sold under the name "Salcare® SC 92" by the company Allied Colloids. A crosslinked methacryloyloxyethyltrimethylammonium chloride homopolymer comprising about 50% by weight of the homopolymer in mineral oil or in a liquid ester can also be used. These dispersions are sold under the names "Salcare® SC 95" and "Salcare® SC 96" by the company Allied Colloids.

(15) Other cationic polymers useful herein are polyalkyleneimines, for example, polyethyleneimines, polymers comprising vinylpyridine or vinylpyridinium units, condensates of polyamines and of epichlorohydrin, quaternary polyureylenes and chitin derivatives.

In at least one embodiment, the cationic polymers may be chosen from the polymers of families (1), (9), (10), (11) and (14) and further, for example, from the polymers comprising repeating units of formulae (W) and (U) below:

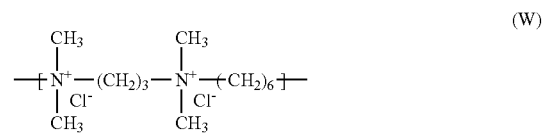

for example, those whose molecular weight, determined by gel permeation chromatography, ranges from 9500 to 9900;

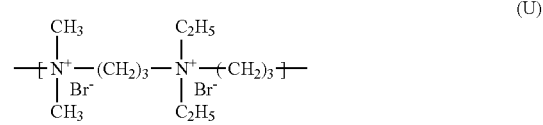

for example, those whose molecular weight, determined by gel permeation chromatography, is about 1200.

The amphoteric polymers useful herein may be chosen from polymers comprising units K and M randomly distributed in the polymer chain, wherein K is a unit derived from a monomer comprising at least one basic nitrogen atom and M is a unit derived from an acidic monomer comprising at least one group chosen from carboxylic and sulfonic groups, or alternatively K and M may independently be groups derived from zwitterionic carboxybetaine or sulfobetaine monomers;

K and M may also be chosen from cationic polymer chains comprising primary, secondary, tertiary or quaternary amine groups, wherein at least one of the amine groups bears a carboxylic or sulfonic group linked via a hydrocarbon-based radical, or alternatively K and M form part of a chain of a polymer comprising an $\alpha,\beta$-dicarboxylic ethylene unit wherein one of the carboxylic groups has been made to react with a polyamine comprising at least one primary or secondary amine groups.

In at least one embodiment, the amphoteric polymers may be chosen from the following polymers:

(1) polymers resulting from the copolymerization of a monomer derived from a vinyl compound bearing a carboxylic group such as, acrylic acid, methacrylic acid, maleic acid, $\alpha$-chloroacrylic acid, and from a substituted vinyl compound comprising at least one basic atom, such as, dialkylaminoalkyl methacrylate and acrylate, dialkylaminoalkyl-methacrylamide and -acrylamide. Such compounds are described in U.S. Pat. No. 3,836,537. Non-limiting mention may also be made of the sodium acrylate/acrylamidopropyl-trimethylammonium chloride copolymer sold under the name POLYQUART KE 3033 by the company Henkel.

The vinyl compound may also be a dialkyldiallylammonium salt such as dimethyldiallylammonium chloride. The copolymers of acrylic acid and of the latter monomer are sold under the names MERQUAT 280, MERQUAT 295 and MERQUAT PLUS 3330 by the company Calgon.

(2) Polymers comprising units derived from:
a) at least one monomer chosen from acrylamides and methacrylamides substituted on the nitrogen with an alkyl radical,
b) at least one acidic comonomer comprising at least one reactive carboxylic group, and
c) at least one basic comonomer such as esters comprising primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides which may be mentioned, for example, are groups in which the alkyl radicals comprise from 2 to 12 carbon atoms, for example, N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen, for example, from acrylic acid, methacrylic acid, crotonic acid, itaconic acid, maleic acid and fumaric acid and alkyl monoesters, having 1 to 4 carbon atoms, of maleic or fumaric acids or anhydrides.

The basic comonomers may be chosen from aminoethyl, butylaminoethyl, N,N'-dimethylaminoethyl and N-tert-butylaminoethyl methacrylates.

The copolymers whose CTFA (4th edition, 1991) name is Octylacrylamide/acrylates/butylaminoethyl methacrylate copolymer such as the products sold under the name AMPHOMER or LOVOCRYL 47 by the company National Starch may, for example, be used.

(3) Polyamino amides that are crosslinked and alkylated partially or totally derived from polyamino amides of general formula:

  (X)

wherein
R$_{19}$ is chosen from
divalent radicals derived from a saturated dicarboxylic acid,
mono- or dicarboxylic aliphatic acids comprising an ethylenic double bond,
esters of a lower alkanol, having 1 to 6 carbon atoms, of these acids, and
radicals derived from the addition of any one of said acids to a bis(primary) or bis(secondary)amine, and
Z is chosen from bis(primary), mono- or bis(secondary) polyalkylene-polyamine radicals chosen from, for example:
a) in an amount of from 60 to 100 mol %, the radical

  (XI)

where x is 2 and p is chosen from 2 or 3, or alternatively x is 3 and p is 2 this radical being derived from diethylenetriamine, from triethylenetetraamine or from dipropylenetriamine;
b) in an amount of from 0 to 40 mol %, the radical (XI) above in which x is 2 and p is 1 and which is derived from ethylenediamine, or the radical derived from piperazine:

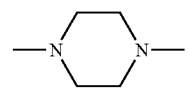

c) in an amount of from 0 to 20 mol %, the —NH—(CH$_2$)$_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids may be, for example, chosen from acids having 6 to 10 carbon atoms, such as adipic acid, 2,2,4-trimethyladipic acid and 2,4,4-trimethyladipic acid, terephthalic acid and acids comprising an ethylenic double bond, for instance acrylic acid, methacrylic acid and itaconic acid.

The alkane sultones used in the alkylation may be, for example, propane sultone or butane sultone, and the salts of the alkylating agents may be, for example, the sodium or potassium salts.

(4) Polymers comprising zwitterionic units of formula:

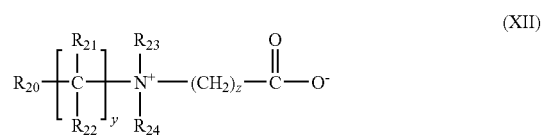  (XII)

wherein
R$_{20}$ is chosen from polymerizable unsaturated groups such as an acrylate, methacrylate, acrylamide or methacrylamide group,
y and z, which may be identical or different, are chosen from integers ranging from 1 to 3, $R_{21}$ and $R_{22}$, which may be identical or different, are chosen from hydrogen atoms, and methyl, ethyl and propyl radicals, $R_{23}$ and $R_{24}$, which may be identical or different, are chosen from hydrogen atoms, and alkyl radicals such that the sum of the carbon atoms in $R_{23}$ and $R_{24}$ does not exceed 10.

The polymers comprising such units can also comprise units derived from nonzwitterionic monomers such as dimethyl or diethylaminoethyl acrylate or methacrylate or alkyl acrylates or methacrylates, acrylamides or methacrylamides or vinyl acetate.

By way of example, non-limiting mention may be made of the copolymer of butyl methacrylate/dimethyl carboxymethylammonioethyl methacrylate such as the product sold under the name DIAFORMER Z301 by the company Sandoz.

(5) Chitosan-based polymers comprising monomer units corresponding to formulae (XIII), (XIV) and (XV) below:

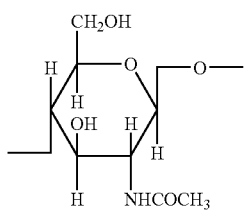
(XIII)

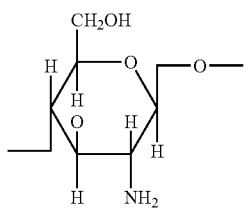
(XIV)

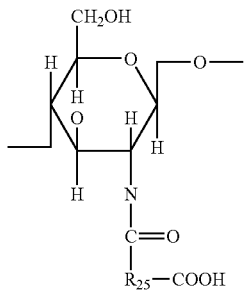
(XV)

the unit (XIII) being present in amounts ranging from 0 to 30%, the unit (XIV) in amounts of 5% to 50% and the unit (XV) in amounts of 30% to 90%, wherein in unit (XV), $R_{25}$ is chosen from radicals of formula:

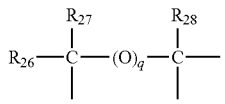

wherein if q is 0, $R_{26}$, $R_{27}$ and $R_{28}$, which may be identical or different, are chosen from
hydrogen atoms,
methyl, hydroxyl, acetoxy or amino residues,
monoalkylamine residues, dialkylamine residues which are optionally interrupted by at least one nitrogen atom and/or optionally substituted with at least one group chosen from amine, hydroxyl, carboxyl, alkylthio and sulfonic groups, alkylthio residues wherein the alkyl group bears an amino residue, wherein at least one of the radicals $R_{26}$, $R_{27}$ and $R_{28}$ is chosen from a hydrogen atom;

or, if q is 1, $R_{26}$, $R_{27}$ and $R_{28}$ are each a hydrogen atom, and also the salts formed by these compounds with bases or acids.

(6) Polymers derived from the N-carboxyalkylation of chitosan, such as N-carboxymethylchitosan or N-carboxybutylchitosan sold under the name "Evalsan" by the company Jan Dekker.

(7) Polymers corresponding to the general formula (XVI) such as those described, for example, in French Patent No. 1 400 366:

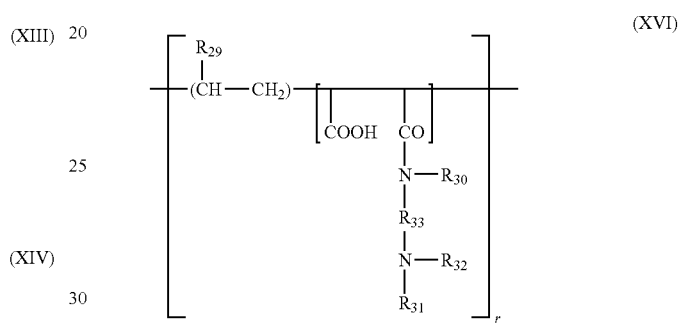
(XVI)

wherein $R_{29}$ is chosen from hydrogen atoms, $CH_3O$, $CH_3CH_2O$ and phenyl radicals, $R_{30}$ is chosen from hydrogen atoms and lower alkyl radicals such as methyl or ethyl, $R_{31}$ is chosen from hydrogen atoms and lower alkyl radicals such as methyl or ethyl, $R_{32}$ is chosen from lower alkyl radicals such as methyl or ethyl and radicals corresponding to the formula: $-R_{33}-N(R_{31})_2$, wherein $R_{33}$ is chosen from $-CH_2-CH_2-$, $-CH_2-CH_2-CH_2-$ and $-CH_2-CH(CH_3)-$ groups, $R_{31}$ having the meanings mentioned above, and r is a number greater than 1.

and also the higher homologues of these radicals and comprising up to 6 carbon atoms.

(8) Amphoteric polymers of the type -D-X-D-X- chosen from:

a) polymers obtained by the action of chloroacetic acid or sodium chloroacetate on compounds comprising at least one unit of formula:

-D-X-D-X-D- (XVII)

wherein D is a radical

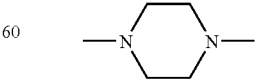

and X is chosen from E and E', wherein E or E', which may be identical or different, are each chosen from divalent radicals which are alkylene radicals with a straight or branched chain comprising up to 7 carbon atoms in the main chain, which are unsubstituted or substituted with hydroxyl groups and which can comprise, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

-D-X-D-X- (XVIII)

wherein D is a radical

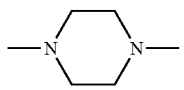

and X is chosen from E and E' and at least once E'; E having the meaning given above and E' being a divalent radical which is an alkylene radical with a straight or branched chain having up to 7 carbon atoms in the main chain, which is unsubstituted or substituted with at least one hydroxyl radical and comprises at least one nitrogen atom, the nitrogen atom being substituted with an alkyl chain which is optionally interrupted with an oxygen atom and necessarily comprising at least one carboxyl function or at least one hydroxyl function and betainized by reaction with chloroacetic acid or sodium chloroacetate.

(9) ($C_1$-$C_5$)alkyl vinyl ether/maleic anhydride copolymers partially modified by semi-amidation with an N,N-dialkylaminoalkylamine such as N,N-dimethylaminopropylamine or by semi-esterification with an N,N-dialkanolamine. These copolymers can also comprise other vinyl comonomers such as vinylcaprolactam.

In one embodiment, the amphoteric polymers used are those of family (1).

In at least one embodiment, the at least one cationic or amphoteric substantive polymer, are present in an amount ranging from 0.01% to 10% by weight relative to the total weight of the composition, for example, from 0.05% to 5% by weight, such as from 0.1% to 3% by weight, relative to the total weight of the composition.

The medium that is suitable for dyeing keratin fibers used herein comprises water or a mixture of water and of at least one organic solvent to dissolve the compounds that are not sufficiently water-soluble. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The solvents may be present in amounts ranging from 1% to 40% by weight, for example, from 5% to 30% by weight, relative to the total weight of the composition.

The composition may also comprise additives that are common in the field, such as, amphoteric or zwitterionic surfactants; organic or mineral thickeners; antioxidants; penetrants; sequestrants; fragrances; buffers; dispersants; conditioning agents other than the cationic or amphoteric substantive polymers described above, for instance cations, or volatile or non-volatile, modified or unmodified silicones; film-forming agents; ceramides; preserving agents; stabilizers; opacifiers.

Needless to say, a person skilled in the art will take care to select this or these optional additional compound(s) such that the advantageous properties intrinsically associated with the composition disclosed herein are not, or are not substantially, adversely affected by the envisaged addition(s).

Also disclosed herein is a process for dyeing keratin materials using the composition disclosed herein.

According to one embodiment, the process comprises applying the composition in the absence of an oxidizing agent, to keratin materials, for example, wet or dry fibers, with or without final rinsing of the composition.

In the case of this embodiment, the composition disclosed herein does not comprise any oxidation dye precursor, but only one or more direct dyes.

In another embodiment, the process comprises applying the composition disclosed herein, in the presence of an oxidizing agent, to wet or dry keratin materials, and then leaving it on for a period that is sufficient to obtain the desired coloration.

According to another embodiment, at least one dye composition disclosed herein and an oxidizing composition are applied to said keratin fibers simultaneously or successively without intermediate rinsing.

In at least one embodiment, the composition applied is a "ready-to-use composition", i.e. a composition obtained by extemporaneous mixing of at least one dye composition as disclosed herein with a composition comprising at least one oxidizing agent.

In this case, the dye composition may comprise at least one oxidation dye precursor. It may also comprise at least one direct dye, when lightening of the keratin fibers is desired in combination with dyeing.

The dye composition may comprise a combination of oxidation dye precursors and of direct dyes.

The oxidizing agent present in the oxidizing composition may be chosen, for example, from hydrogen peroxide, urea peroxide, alkali metal bromates, persalts such as perborates and persulfates, and enzymes such as peroxidases and two-electron or four-electron oxidoreductases. In one embodiment, the oxidizing agent is hydrogen peroxide.

The oxidizing agent may be present in an amount ranging from 1% to 40% by weight, relative to the total weight of the ready-to-use composition, for example, from 1% to 20% by weight, relative to the total weight of the ready-to-use composition.

In one embodiment, the oxidizing composition used is an aqueous composition and may be in the form of a solution or an emulsion.

In another embodiment, the composition free of oxidizing agent is mixed with about 0.5 to 10 weight equivalents of the oxidizing composition.

It should be noted that the pH of the ready-to-use composition may range, for example, from 3 to 12, for example, from 4 to 1 1 and further, for example, from 6.5 to 10.5.

The pH of the ready-to-use composition may be adjusted using a basifying or acidifying agent chosen, for example, from those mentioned previously.

Where the composition is applied in the presence of an oxidizing agent, for example, the process may comprise a preliminary step comprising separately storing the at least one dye composition disclosed herein and a composition comprising at least one oxidizing agent in a medium that is suitable for dyeing human keratin fibers, and then mixing them together at the time of use, before applying this mixture to the wet or dry keratin materials.

In the presence or absence of oxidizing agent, the time required to develop the coloration ranges from a few seconds to 60 minutes, for example, from 1 to 50 minutes.

The temperature required to develop the coloration ranges from room temperature (15 to 25° C.) to 250° C., for example, from room temperature to 180° C. and further, for example, from room temperature to 60° C.

Once the time required to develop the coloration has elapsed, the composition may be, in at least some embodiments, removed. Removal may take place in a conventional manner, either by performing at least one rinsing operation, or by performing at least one washing and rinsing operations, or by performing a combination thereof. Finally, the keratin materials may be dried or are left to dry.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments disclosed herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosed embodiments are approximations, unless otherwise indicated the numerical values set forth in the specific examples are reported as precisely as possible. Any numerical value, however, inherently contains certain errors necessarily resulting from the standard deviation found in their respective testing measurements.

The embodiments disclosed herein are illustrated in greater detail by the non-limiting example described below.

EXAMPLES

The dye compositions below as disclosed herein were prepared (amounts expressed in grams):

| | A | B |
|---|---|---|
| Stearyl alcohol (Lanette 18; from Cognis) | / | 5 |
| Double-distilled pure cetyl alcohol (Lanette 16; from Cognis) | 10.2 | 5.2 |
| Polyglycerolated (2 mol) oleyl alcohol | 4 | / |
| Oxyethylenated (10 OE) oleyl alcohol (Brij 96 V; from Uniqema) | / | 1.5 |
| Oxyethylenated (30 OE) oleyl alcohol (Eumulgin O 30; from Cognis) | / | 2.5 |
| Sodium laurylpolyglucoside (n = 1.4) ether carboxylate at 30% in water (Plantapon LGC Sorb; from Cognis) | 0.8 | / |
| Glyceryl stearate (Tegin 6070; from Goldschmidt) | 5.8 | 5.8 |
| Distearyl ether (Cutina STE; from Cognis) | 1.8 | 1.8 |
| Oleic acid | 2.73 | 2.73 |
| Pure monoethanolamine | 0.52 | 0.52 |
| Polydimethyldiallylammonium chloride at 40% in water, non-stabilized (Polyquaternium-6) | / | 2 |
| Sodium metabisulfite | 0.71 | 0.71 |
| Ammonium thiolactate as an aqueous 58% solution | / | / |
| Ascorbic acid | 0.25 | 0.25 |
| Titanium oxide (untreated anatase) coated with polydimethylsiloxane (98/2) | 0.15 | 0.15 |
| Citric acid | 0.31 | 0.31 |
| Aqueous ammonia (20% ammonia) | 11.1 | 11.1 |
| 1-Hydroxy-4-aminobenzene | 0.545 | 0.545 |

-continued

| | A | B |
|---|---|---|
| 1-Methyl-2-hydroxy-4-aminobenzene | 0.615 | 0.615 |
| Fragrance | 0.95 | 0.95 |
| Deionized water | 59.52 | 58.32 |

The above dye compositions were mixed, at the time of use, in a plastic bowl and for 2 minutes, with an aqueous oxidizing composition comprising 6% hydrogen peroxide, at a rate of 1 part of dye composition per 1.5 parts of oxidizing composition. The mixing was quick and easy.

The mixtures obtained were applied to locks of natural hair comprising 90% white hairs, and were left on for 20 minutes. The applications were quick and easy. The product stayed in place perfectly, did not run, and spread well from the root to the end.

The locks were then rinsed with water, washed with a standard shampoo, rinsed again with water, and then dried and disentangled. The mixtures were satisfactorily removed on rinsing.

The hair was dyed in a strong coppery red shade. Furthermore, the hair was not coarse.

What is claimed is:

1. A dye composition comprising, in a medium that is suitable for dyeing keratin fibers:
   at least one dye chosen from oxidation dye precursors and direct dyes;
   at least one fatty alcohol;
   at least one fatty acid ester of glycerol;
   at least one ether of formula R—O—R', in which R and R', which may be identical or different, are each chosen from linear or branched $C_{10}$-$C_{30}$ alkyl radicals and $C_{10}$-$C_{30}$ alkenyl radicals, R and R' being chosen such that the ether of formula R—O—R' is solid at a temperature of less than or equal to 30° C.;
   at least one surfactant chosen from nonionic surfactants and anionic surfactants;
   wherein said composition comprises water in an amount of at least 55% by weight, relative to the total weight of the composition.

2. A composition according to claim 1, wherein water is present in an amount of at least 60% by weight, relative to the total weight of the composition.

3. A composition according to claim 1, wherein the at least one fatty alcohol is present in an amount ranging from 0.1% to 30% by weight, relative to the weight of the composition.

4. A composition according to claim 1, wherein the at least one fatty acid ester of glycerol is chosen from esters of oleic acid, lauric acid, palmitic acid, myristic acid, behenic acid, stearic acid, linoleic acid, linolenic acid, capric acid, arachidic acid and arachidonic acid, and mixtures thereof.

5. A composition according to claim 1, wherein the at least one fatty acid ester of glycerol is present in an amount ranging from 0.1% to 20% by weight, relative to the total weight of the composition.

6. A composition according to claim 1, wherein R and R', which may be identical or different, are chosen from radicals derived from oleyl alcohol (C18), lauryl alcohol (C12), palmityl alcohol (C16), myristyl alcohol (C14), behenyl alcohol (C22), stearyl alcohol (C18), linoleyl alcohol (C18), linolenyl alcohol (C18) and arachidyl alcohol (C20).

7. A composition according to claim 1, wherein the at least one ether of formula R—O—R' is present in an amount ranging from 0.1% to 10% by weight, relative to the total weight of the composition.

8. A composition according to claim 1, wherein the at least one nonionic surfactant is chosen from:
   oxyalkylenated or glycerolated fatty alcohols;
   oxyalkylenated alkylphenols wherein the alkyl chain is $C_8$-$C_{18}$;
   oxyalkylenated or glycerolated fatty amides;
   oxyalkylenated plant oils;
   optionally oxyalkylenated fatty acid esters of sorbitan;
   optionally oxyalkylenated fatty acid esters of sucrose;
   fatty acid esters of polyethylene glycol;
   ($C_6$-$C_{30}$)alkylpolyglycosides;
   N-($C_6$-$C_{30}$)alkylglucamine derivatives;
   amine oxides;
   copolymers of ethylene oxide and of propylene oxide; and
   mixtures thereof.

9. A composition according to claim 8, wherein the amine oxides are chosen from ($C_{10}$-$C_{14}$)alkylamine oxides and N-acylaminopropylmorpholine oxides.

10. A composition according to claim 1, wherein the at least one nonionic surfactant is chosen from oxyalkylenated fatty alcohols and from glycerolated fatty alcohols.

11. A composition according to claim 1, wherein the at least one anionic surfactant is chosen from:
   ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates, monoglyceride sulfates;
   ($C_6$-$C_{30}$)alkylsulfonates, ($C_6$-$C_{30}$)alkylamide sulfonates, ($C_6$-$C_{30}$)alkylaryl sulfonates, α-olefin sulfonates, paraffin sulfonates;
   ($C_6$-$C_{30}$)alkyl phosphates;
   ($C_6$-$C_{30}$)alkyl sulfosuccinates, ($C_6$-$C_{30}$)alkyl ether sulfosuccinates, ($C_6$-$C_{30}$)alkylamide sulfosuccinates;
   ($C_6$-$C_{30}$)alkyl sulfoacetates;
   ($C_6$-$C_{24}$)acyl sarcosinates;
   ($C_6$-$C_{24}$)acyl glutamates;
   ($C_6$-$C_{30}$)alkylpolyglycoside carboxylic ethers; ($C_6$-$C_{30}$) alkylpolyglycoside sulfosuccinates;
   ($C_6$-$C_{30}$)alkyl sulfosuccinamates;
   ($C_6$-$C_{24}$)acyl isethionates;
   N—($C_6$-$C_{24}$)acyl taurates;
   $C_6$-$C_{30}$ fatty acid salts;
   ($C_8$-$C_{20}$)acyl lactylates;
   ($C_6$-$C_{30}$)alkyl-D-galactoside uronic acid salts;
   polyoxyalkylenated ($C_6$-$C_{30}$)alkyl ether carboxylic acid salts, polyoxyalkylenated ($C_6$-$C_{30}$)alkylaryl ether carboxylic acid salts, polyoxyalkylenated ($C_6$-$C_{30}$)alkylamido ether carboxylic acid salts;
   and mixtures thereof.

12. A composition according to claim 1, wherein the at least one anionic surfactant is chosen from fatty acid salts and surfactants comprising at least one sulfate group, or a mixture thereof.

13. A composition according to claim 1, wherein the at least one surfactant chosen from nonionic surfactants and anionic surfactants is present in an amount ranging from 0.01% to 40% by weight, relative to the total weight of the composition.

14. A composition according to claim 1, wherein the composition comprises at least one fatty substance other than the at least one fatty alcohol.

15. A composition according to claim 14, wherein the at least one fatty substance other than the at least one fatty alcohol is chosen from non-oxyalkylenated, non-glycerolated fatty acid amides, carboxylic acid monoesters and polyesters, mineral oils and plant oils, and mixtures thereof.

16. A composition according to claim 1, wherein the at least one oxidation dye precursor is chosen from oxidation bases and couplers, and mixtures thereof.

17. A composition according to claim 16, wherein the oxidation base(s) are present in an amount ranging from 0.0005% to 12% by weight, relative to the weight of the composition.

18. A composition according to claim 16, wherein the coupler(s) are present in an amount ranging from 0.0001% to 15% by weight, relative to the weight of the composition.

19. A composition according to claim 1, wherein the at least one direct dye is present in an amount ranging from 0.0005% to 15% by weight, relative to the weight of the composition.

20. A composition according to claim 1, wherein the composition comprises at least one basifying agent.

21. A composition according to claim 20, wherein the at least one basifying agent is chosen from aqueous ammonia, alkanolamines and combinations of $C_2$-$C_{10}$ alkanolamines with alkali metal or alkaline-earth metal silicates.

22. A composition according to claim 1, wherein the composition further comprises at least one cationic or amphoteric substantive polymer.

23. A composition according to claim 22, wherein the at least one cationic or amphoteric substantive polymer is present in an amount ranging from 0.01% to 10% by weight, relative to the weight of the composition.

24. A composition according to claim 1, wherein the composition further comprises at least one oxidizing agent.

25. A process for dyeing keratin fibers, comprising
   applying to wet or dry keratin fibers a dye composition comprising, in a medium that is suitable for dyeing keratin fibers:
      at least one dye chosen from oxidation dye precursors and direct dyes;
      at least one fatty alcohol;
      at least one fatty acid ester of glycerol;
      at least one ether of formula R—O—R', wherein R and R', which may be identical or different, are each chosen from linear or branched $C_{10}$-$C_{30}$ alkyl and alkenyl radicals, and are chosen such that the ether of formula R—O—R' is solid at a temperature of less than or equal to 30° C.;
      at least one surfactant chosen from nonionic surfactants and anionic surfactants;
   wherein said composition comprises water in an amount of at least 55% by weight, relative to the total weight of the composition.

26. A process for dyeing keratin fibers, comprising
   applying to wet or dry fibers, a dye composition in the presence of at least one oxidizing composition, wherein said oxidizing composition is applied simultaneously with or successively to the dye composition without intermediate rinsing,
   said dye composition comprising, in a medium that is suitable for dyeing keratin fibers:
      at least one dye chosen from oxidation dye precursors and direct dyes;
      at least one fatty alcohol;
      at least one fatty acid ester of glycerol;
      at least one ether of formula R—O—R', wherein R and R', which may be identical or different, are each chosen from linear or branched $C_{10}$-$C_{30}$ alkyl and alkenyl radicals, wherein the ether of formula R—O—R' is solid at a temperature of less than or equal to 30° C.;
      at least one surfactant chosen from nonionic surfactants and anionic surfactants;

wherein water is present in an amount of at least 55% by weight, relative to the weight of the composition leaving the mixture on the fibers, and rinsing the fibers.

27. A process for dyeing keratin fibers, comprising applying to said wet or dry keratin fibers, in the presence of at least one oxidizing composition, a dye composition, wherein said at least one oxidizing agent is mixed with the dye composition before application, said dye composition comprising, in a medium that is suitable for dyeing keratin fibers:
- at least one dye chosen from oxidation dye precursors and direct dyes;
- at least one fatty alcohol;
- at least one fatty acid ester of glycerol;
- at least one ether of formula R—O—R', wherein R and R', which may be identical or different, are each chosen from linear or branched $C_{10}$-$C_{30}$ alkyl and alkenyl radicals, wherein the ether of formula R—O—R' is solid at a temperature of less than or equal to 30° C.;
- at least one surfactant chosen from nonionic surfactants and anionic surfactants;

wherein water is present in an amount of at least 55% by weight, relative to the weight of the composition leaving the mixture on the fibers, and rinsing the fibers.

28. A multi-compartment device that may be used for dyeing keratin fibers, comprising a first compartment comprising a dye composition comprising, in a medium that is suitable for dyeing keratin fibers:
- at least one dye chosen from oxidation dye precursors and direct dyes;
- at least one fatty alcohol;
- at least one fatty acid ester of glycerol;
- at least one ether of formula R—O—R', wherein R and R', which may be identical or different, are each chosen from linear or branched $C_{10}$-$C_{30}$ alkyl and alkenyl radicals, and are chosen such that the ether of formula R—O—R' is solid at a temperature of less than or equal to 30° C.;
- at least one surfactant chosen from nonionic surfactants and anionic surfactants;

wherein said composition comprises water in an amount of at least 55% by weight, relative to the total weight of the composition, and comprising a second compartment comprising an oxidizing composition.

* * * * *